United States Patent
Vacanti et al.

(10) Patent No.: US 9,999,638 B2
(45) Date of Patent: *Jun. 19, 2018

(54) SUBPOPULATIONS OF SPORE-LIKE CELLS AND USES THEREOF

(71) Applicant: VBI Technologies, L.L.C., Uxbridge, MA (US)

(72) Inventors: Martin P. Vacanti, Manhattan, KS (US); Charles A. Vacanti, Uxbridge, MA (US)

(73) Assignee: VBI Technologies, L.L.C., Uxbridge, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/272,797

(22) Filed: Sep. 22, 2016

(65) Prior Publication Data

US 2017/0007647 A1  Jan. 12, 2017

Related U.S. Application Data (60) Division of application No. 14/845,641, filed on Sep. 4, 2015, now Pat. No. 9,663,765, which is a division
(Continued)

(51) Int. Cl.

| | |
|---|---|
| *A61K 35/407* | (2015.01) |
| *C12N 5/074* | (2010.01) |
| *C12N 5/071* | (2010.01) |
| *C12N 5/0797* | (2010.01) |
| *C12N 5/0789* | (2010.01) |
| *C12N 5/0775* | (2010.01) |
| *C12N 5/079* | (2010.01) |
| *C12N 5/077* | (2010.01) |
| *A61K 35/22* | (2015.01) |
| *A61K 35/28* | (2015.01) |
| *A61K 35/30* | (2015.01) |
| *A61K 35/34* | (2015.01) |
| *A61K 35/42* | (2015.01) |
| *A61K 35/12* | (2015.01) |

(52) U.S. Cl.
CPC ............ *A61K 35/407* (2013.01); *A61K 35/22* (2013.01); *A61K 35/28* (2013.01); *A61K 35/30* (2013.01); *A61K 35/34* (2013.01); *A61K 35/42* (2013.01); *C12N 5/0607* (2013.01); *C12N 5/0614* (2013.01); *C12N 5/0618* (2013.01); *C12N 5/0623* (2013.01); *C12N 5/0647* (2013.01); *C12N 5/0652* (2013.01); *C12N 5/0658* (2013.01); *C12N 5/0668* (2013.01); *C12N 5/0669* (2013.01); *C12N 5/0672* (2013.01); *C12N 5/0688* (2013.01); *A61K 2035/124* (2013.01); *C12N 2501/11* (2013.01); *C12N 2501/115* (2013.01); *C12N 2501/392* (2013.01); *Y10T 436/101666* (2015.01); *Y10T 436/25375* (2015.01)

(58) Field of Classification Search
CPC ...... A61K 35/407; A61K 35/22; A61K 35/28; A61K 35/30; A61K 35/34; A61K 35/42; A61K 2035/124; C12N 5/0669; C12N 5/0607; C12N 5/0614; C12N 5/0623; C12N 5/0647; C12N 5/0618; C12N 5/0658; C12N 5/0668; C12N 5/0688; C12N 5/0652; C12N 5/0672; C12N 2501/11; C12N 2501/115; C12N 2501/392; C12N 2035/124; Y10T 436/25375; Y10T 436/101666

See application file for complete search history.

(56) References Cited

U.S. PATENT DOCUMENTS

| | | |
|---|---|---|
| 4,060,081 A | 11/1977 | Yannas |
| 4,188,373 A | 2/1980 | Krezanoski |

(Continued)

FOREIGN PATENT DOCUMENTS

| | | |
|---|---|---|
| EP | 0361957 | 4/1990 |
| WO | 9206702 | 4/1992 |

(Continued)

OTHER PUBLICATIONS

Torella et al. The Cardiac System Cell: The Adult Mammalian Heart Harbours Oct.4pos Cardiac Stem Cells With Very Broad Developmental Potential, Circulation Abstract 1567, 114: (II)_303 (2006).*
Cyranoski, et al., "Cell-induced stress", Nature, 511:140-3 (2014).
Ahmed, et al., "BDNF enhances the differentiation but not the survival of CNS stem cell-derived neuronal properties" The Journal of Neuroscience 15 (8):5765-5778 (1995).
Bouwens and Blay, "Islet morphogenesis and stem cell markers in rat pancreas" The Journal of Histochemistry and Cytochemistry 44(9): 947-951 (1996).
Burke, et al., "Successful use of a physiologically acceptable artificial skin in the treatment of extensive burn injury", Ann. Surg., 194:413-428 (1981).

(Continued)

*Primary Examiner* — Gailene Gabel
(74) *Attorney, Agent, or Firm* — Pabst Patent Group, LLP (57) ABSTRACT

Subpopulations of spore-like cells expressing specific cell surface and gene expression markers are provided. In one embodiment, the cells express at least one cell surface or gene expression marker selected from the group consisting of Oct4, nanog, Zfp296, cripto, Gdf3, UtF1, Ecat1, Esg1, Sox2, Pax6, nestin, SCA-1, CD29, CD34, CD90, B1 integrin, cKit, SP-C, CC10, SF1, DAX1, and SCG10. Also provided are methods for purifying a subpopulation of spore-like cells of interest from a population of spore-like cells, and methods for inducing differentiation of the isolated spore-like cells into cells of endodermal, mesodermal or ectodermal origin. The spore-like cells can be used to generate cells originating from all three germ layers and can be used to treat a patient who has a deficiency of functional cells in any of a wide variety of tissues, including the retina, intestine, bladder, kidney, liver, lung, nervous system, or endocrine system.

10 Claims, 1 Drawing Sheet

Related U.S. Application Data of application No. 14/025,528, filed on Sep. 12, 2013, now Pat. No. 9,145,545, which is a continuation of application No. 12/944,342, filed on Nov. 11, 2010, now Pat. No. 8,551,775.

(60) Provisional application No. 61/260,607, filed on Nov. 12, 2009.

(56) References Cited

U.S. PATENT DOCUMENTS

| | | |
|---|---|---|
| 4,191,747 A | 3/1980 | Scheicher |
| 4,352,883 A | 10/1982 | Lim |
| 4,419,936 A | 12/1983 | Coates |
| 4,474,751 A | 10/1984 | Haslam |
| 4,474,752 A | 10/1984 | Haslam |
| 4,474,753 A | 10/1984 | Haslam |
| 4,478,822 A | 10/1984 | Haslam |
| 4,846,835 A | 7/1989 | Grande |
| 4,997,443 A | 3/1991 | Walthall |
| 5,041,138 A | 8/1991 | Vacanti |
| 5,071,644 A | 12/1991 | Viegas |
| 5,082,670 A | 1/1992 | Gage |
| 5,126,141 A | 6/1992 | Henry |
| 5,192,326 A | 3/1993 | Bao |
| 5,277,911 A | 1/1994 | Viegas |
| 5,292,516 A | 3/1994 | Viegas |
| 5,292,655 A | 3/1994 | Wille, Jr. |
| 5,294,446 A | 3/1994 | Schlameus |
| 5,298,260 A | 3/1994 | Viegas |
| 5,300,295 A | 4/1994 | Viegas |
| 5,306,501 A | 4/1994 | Viegas |
| 5,318,780 A | 6/1994 | Viegas |
| 5,405,366 A | 4/1995 | Fox |
| 5,410,016 A | 4/1995 | Hubbell |
| 5,411,883 A | 5/1995 | Boss |
| 5,443,950 A | 8/1995 | Naughton |
| 5,512,600 A | 4/1996 | Mikos |
| 5,514,378 A | 5/1996 | Mikos |
| 5,514,379 A | 5/1996 | Weissleder |
| 5,523,226 A | 6/1996 | Wheeler |
| 5,529,914 A | 6/1996 | Hubbell |
| 5,567,612 A | 10/1996 | Vacanti |
| 5,575,815 A | 11/1996 | Slepian |
| 5,578,485 A | 11/1996 | Naughton |
| 5,589,376 A | 12/1996 | Anderson |
| 5,593,974 A | 1/1997 | Rosenberg |
| 5,667,778 A | 9/1997 | Atala |
| 5,696,175 A | 12/1997 | Mikos |
| 5,709,854 A | 1/1998 | GriffithGime |
| 5,716,404 A | 2/1998 | Vacanti |
| 5,736,372 A | 4/1998 | Vacanti |
| 5,736,396 A | 4/1998 | Bruder |
| 5,750,376 A | 5/1998 | Weiss |
| 5,750,397 A | 5/1998 | Tsukamoto |
| 5,753,506 A | 5/1998 | Johe |
| 5,759,830 A | 6/1998 | Vacanti |
| 5,762,926 A | 6/1998 | Gage |
| 5,766,948 A | 6/1998 | Gage |
| 5,770,193 A | 6/1998 | Vacanti |
| 5,770,417 A | 6/1998 | Vacanti |
| 5,780,300 A | 7/1998 | ArtavanisTsakonas |
| 5,786,216 A | 7/1998 | Dionne |
| 5,795,790 A | 8/1998 | Schinstine |
| 5,800,811 A | 9/1998 | Hall |
| 5,804,178 A | 9/1998 | Vacanti |
| 5,824,489 A | 10/1998 | anderson |
| 5,827,735 A | 10/1998 | Young |
| 5,827,742 A | 10/1998 | Scadden |
| 5,830,651 A | 11/1998 | Cauley |
| 5,834,029 A | 11/1998 | Bellamkonda |
| 5,851,832 A | 11/1998 | Weiss |
| 5,855,610 A | 1/1999 | Vacanti |
| 5,891,455 A | 4/1999 | Sittinger |
| 5,932,459 A | 8/1999 | Sittinger |
| 5,944,754 A | 8/1999 | Vacanti |
| 5,994,754 A | 11/1999 | Hayashi |
| 6,027,744 A | 2/2000 | Vacanti |
| 7,060,492 B2* | 6/2006 | Vacanti ............... C12N 5/0602 435/1.1 |
| 7,310,147 B2 | 12/2007 | Jiang |
| 7,575,921 B2* | 8/2009 | Vacanti ............... C12N 5/0602 424/93.21 |
| 7,964,394 B2* | 6/2011 | Vacanti ............... C12N 5/0602 424/93.21 |
| 8,551,775 B2* | 10/2013 | Vacanti ............... C12N 5/0607 422/73 |
| 9,145,545 B2* | 9/2015 | Vacanti ............... C12N 5/0607 |
| 2003/0008351 A1 | 1/2003 | Deisher |
| 2004/0033598 A1 | 2/2004 | Vacanti |
| 2004/0057942 A1 | 3/2004 | Vacanti |
| 2009/0275067 A1 | 11/2009 | Taniguchi |
| 2015/0376576 A1* | 12/2015 | Vacanti ............... C12N 5/0607 435/7.21 |

FOREIGN PATENT DOCUMENTS

| | | |
|---|---|---|
| WO | 9316687 | 9/1993 |
| WO | 9324627 | 12/1993 |
| WO | 9425079 | 11/1994 |
| WO | 9425080 | 11/1994 |
| WO | 9615226 | 5/1996 |
| WO | 9640304 | 12/1996 |
| WO | 9715655 | 5/1997 |
| WO | 9740137 | 10/1997 |
| WO | 9741208 | 11/1997 |
| WO | 9746665 | 12/1997 |
| WO | 9822155 | 5/1998 |
| WO | 9823761 | 6/1998 |
| WO | 9824385 | 6/1998 |
| WO | 9830678 | 7/1998 |
| WO | 0149113 | 7/2001 |

OTHER PUBLICATIONS

Cornelius, et al., "In Vitro-Generation of Islets in Long-Term Cultures of Pluripotent Stem Cells From Adult Mouse Pancreas," Horm. Metab. Res., 29(6): 271-277 (1997).

Craig, et al., "In Vivo Growth Factor Expansion of Endogenous Subependymal Neural Precursor Cell Populations in the Adult Mouse Brain," The Journal of Neuroscience, 16:2649-2658 (1996).

Dabeva, et al., "Differentiation of Pancreatic Epithelial Progenitor Cells into Hepatocytes Following Transplantation into Rat Liver," Proc. Natl. Acad. Sci., 94:7356-7361 (1997).

Davis, et al., "A Self-Renewing Multipotent Stem Cell in Embryonic Rat Cerebral Cortex," Nature, 372:263-269 (1994).

Ehtesham, et al., "The use of interleukin 12-secreting neural stem cells for the treatment of intracranial glioma", Cancer Reserves, 62 (20):5657-63 (2002).

Ehtesham, et al., "Treatment of intracranial glioma with in situ interferon-gamma and tumor necrosis factor-alpha gene transfer", Cancer Therapy, 9 (11):925-934 (2002).

Emura, "Stem cells of the respiratory epithelium and their in vitro cultivation" In Vitro Cell Dev. Biol. Anim. 33(1): 3-14 (1997).

Farriol, et al., "Epidermal growth factor excretion in burned rats", Burns, 20:496-498 (1994).

Ferrari, et al., "Muscle regeneration by bone marrow-derived myogenic progenitors" Science 279: 1528-1530 (1998).

Ferringa, et al., "Regeneration of Corticospinal Axons in the Rat", Annals of Neurology, 2:315-321 (1977).

Frederiken and McKay, "Proliferation and differentiation of rat neuroepithelial precursor cells in vivo", J. Neurosci., 8:1144-51 (1988).

Gage, "Mammalian neural stem cells" Science, 287:1433-1438 (2000).

Gage, et al., "Survival and Differentiation of Adult Neuronal Progenitor Cells Transplanted to the Adult Brain", Proc. Natl. Acad. Sci. USA, 92:11879-11883 (1995).

Gritti, et al., "Multipotent stem cells from the adult mouse brain proliferate and self-renew in response to basic fibroblast growth factor" The Journal of Neuroscience 16(3): 1091-1100 (1996).

(56) References Cited

OTHER PUBLICATIONS

Guidry, "Isolation and Characterization of Porcine Müller Cells. Myofibroblastic Dedifferentiation in Culture," Invest. Ophthalmol. Vis. Sci., 37(5): 740-52 (1996).
Haisch, et al., Tissue engineering humanen Knorpelgewebes fur die rekonstruktive Chirurgie unter Verwendung biokomapatibler resorblerbarer fibringel-und polymervliesstrukturen, HNO, 44:624-9 (1996) (Abstract).
Jackson, et al., "Hematopoietic potential of stem cells isolated from murine skeletal muscle" Proceedings of the National Academy of Sciences, 96(25): 14482-14486 (1999).
Johansson, et al., "Identification of a neural stem cell in the adult mammalian central nervous system" Cell 96: 25-34 (1999).
Kanatsu-Shinohara, et al., "Generation of pluripotent stem cells from neonatal mouse testis", Cell, 1001-1012 (2004).
Lachyanker, et al., "Embryonic Precursor Cells that Express Trk Receptors: Induction of Different Cell Fates by NGF, BDNF, NT-3, and CNTF", Experimental Neurology, 144:350-360 (1997).
Langer, et al., "Tissue Engineering," Science, 260:920-926 (1993).
Levine and Beivanlou, "GDF3, a BMP inhibitor, regulates cell fate in stem cells and early embryos", Developement, 133:209-16 (2005).
Liau, et al., "Treatment of intracranial gliomas with bone marrow-derived dendritic cells pulsed with tumor antigens", J. of Neuro. 90 (6):115-24 (1999).
Mandel, et al., "Fetal Islet Xenotransplantation in Rodents and Primates," J. Mol. Med., 77:155-160 (1999).
Mann, et al., "Stem and iPS cell selection: quantitation of surface marker (SSEA1) and intracellular GFP", Nature Methods, i-ii, (2007).
Martin, "Isolation of a pluripotent cell line from early mouse embryos cultured in medium conditioned by teratocarcinoma stem cells", Proc Natl Acad Sci U S A., 78:7634-7638 (1981).
McDonald, et al., "Transplanted embryonic stem cells survive, differentiate and promote recovery in injured rat spinal cord" Nature Medicine 5(12): 1410-1412 (1999).
Mehler, et al., "Cytokines regulate the cellular phenotype of developing neural lineage species" Int. J. Devl. Neuroscience 13(3/4): 213-240 (1995).
Mezey, et al., "Turning blood into brain: Cells bearing neuronal antigens generated in vivo from bone marrow", Science, 290: 1779-1782 (2000).
Moeller, et al., "Differential expression of neural cell adhesion molecule and cadherins in pancreatic Islets, glucagonomas, and insulinomas," Mol. Endocrinology, 6:1332-1342 (1992).
Moore, et al., "Vascular function and tissue injury in murine skin following hyperthermia and photodynamic therapy, alone and in combination", Br. J. Cancer, 66:1037-1043 (1992).
Morshead, et al., "Neural Stem Cells in the Adult Mammalian Forebrain: A Relatively Quiescent Subpopulation of Subependymal Cells," Neuron, 13:1071-1082 (1994).
Murphy, et al., "Neural stem cells" Journal of Investigative Dermatology Symposium Proceedings 2(1): 8-13 (1997).
Niwa, "How is pluripotency determined and maintained", Development, 134:635-646 (2007).
Niwa, "Molecular mechanism to maintain stem cell renewal of ES cells", Cell Structure and Function, 26(3):137-148 (2001).
Notter, et al., "Neuronal properties of monkey adrenal medulla in vitro" Cell Tissue Research 244: 69-76 (1986).
Ourednik, et al., "Neural stem cells display an inherent mechanism for rescuing dysfunctional neurons", Nature Biotechnol., 20(11):1103-1110 (2002).
Palmer and Gage, "FGF-2 responsive neuronal progenitors reside in proliferative and quiescent regions of the adult rodent brain" Molecular and Cellular Neuroscience 6: 474-486 (1995).
Palmer and Gage, "The adult rat hippocampus contains primordial neural stem cells" Molecular and Cellular Neuroscience 8: 389-404 (1997).
Pan, et al., "Stem cell pluripotency and transcription factor Oct4", Cell Res., 12:321-329 (2002).
Pittenger, et al., "Multilineage potential of adult human mesenchymal stem cells" Science 284: 143-147 (1999).
Potten, "Stem cells in gastrointestinal epithelium: numbers, characteristics and death", Philos Trans R Soc Lond B Biol Sci., 353:821-830 (1998).
Prockop, "Marrow stromal cells as stem cells for nonhematopoietic tissues" Science 276: 71-74 (1997).
Random House Websters College Dictionary Definition of "spore". 2002. New York Random House, p. 1294.
Ray, et al., "Proliferation, Differentiation, and Long-Term Culture of Primary Hippocampal Neurons," Proc. Natl. Acad. Sci. USA, 90:3602-3606 (1993).
Ray, et al., "Spinal Cord Neuroblasts Proliferate in Response to Basic Fibroblast Growth Factor," The Journal of Neuroscience, 14:3548-3564 (1994).
Reyes and Vetfaillie, "Characterization of multipotent adult progenitor cells, a subpopulation of mesenchymal stem cells", Ann NY Acad Sci., 938:231-235 (2001).
Reyes, et al., "Purification and ex vivo expansion of postnatal human marrow mesodermal progenitor cells", Blood, 98(9):2615-2625 (2001).
Reynolds, et al., "A Multipotent EGF-Responsive Striatal Embryonic Progenitor Cell Produces Neurons and Astrocytes," The Journal of Neuroscience, 12:4565-4574 (1992).
Reynolds, et al., "Clonal and Population Analyses Demonstrate that an EGF-Responsive Mammalian Embryonic CNS Precursor is a Stem Cell," Developmental Biology, 175:1-13 (1996).
Reynolds, et al., "Generation of Neurons and Astrocytes from Isolated Cells of the Adult Mammalian Central Nervous System," Science, 255:1707-1710 (1992).
Roskams, et al., "Undifferentiated progenitor cells in focal nodular hyperplasia of the liver" Histopathology 28(4): 291-299 (1996).
Santa-Olalla and Covarrubias, "Epidermal growth factor (EGF), transforming growth factor-a (TGF-a), and basic fibroblast growth factor (bFGF) differential influence neural precursor cells of mouse embryonic mesencephalon" Journal of Neuroscience Research 42: 172-183 (1995).
Schuldiner, et al., "Effects of eight growth factors on the differentiation of cells derived from human embryonic stem cells", Proc Natl Acad Sci USA, 97:11307-11312 (2000).
Schwartz, et al., "Multipotent adult progenitor cells from bone marrow differentiate into functional hepatocyte-like cells", Clin Invest, 109:1291-1302 (2002).
Seidl and Unsicker, "Survival and neuritic growth of sympathoadrenal (chromaffin) precursor cells in vitro" Int. J. Dev. Neuroscience 7(5): 465-473 (1989).
Shihabuddin, et al., "Induction of Mature Neuronal Properties in Immortalized Neuronal Precursor Cells Following Grafting into the Neonatal CNS," Journal of Neurocytology, 25:101-111 (1996).
Shihabuddin, et al., "The Adult CNS Retains the Potential to Direct Region-Specific Differentiation of a Transplanted Neuronal Precursor Cell Line," The Journal of Neuroscience, 15:6666-6678 (1995).
Shihabuddin, et al., "FGF-2 is sufficient to isolate progenitors found in the adult mammalian spinal cord," Exp. Neurol. 148(2): 577-586 (1997).
Sittinger, "Tissue engineering: kunstilcher gewerbeersatz aus vitalen komponenten" Laryngo-Rhino-Otol., 74: 695-6 (1995) (Abstract).
Stewart, et al., "Non-neural adult stem cells: tools for brain repair", Bioessays, 24 (8): 708-13 (2002).
Strizzi, "Cripto-1: a multifunctional modulator during embryogenesis and oncogenesis", Oncogene, 24:5731-5741 (2005).
Suhonen, et al., "Differentiation of Adult Hippocompus-Derived Progenitors into Olfactory Neurons in Vivo," Nature, 383:624-627 (1996).
Tanihuchi, et al., "Constant Delivery of Proinsulin by Encapsulation of Transfected Cells, " Journal of Surgical Res., 70:41-45 (1997).
Taupin and Gage, "Adult neurogenesis and neural stem cells of the central nervous system in mammals" Journal of Neuroscience Research 69(6): 745-749 (2002).

(56) References Cited

OTHER PUBLICATIONS

Taylor, et al., "Widespread Engraftment of Neural Progenitor and Stem-Like Cells Throughout the Mouse Brain," Transplantation Proceedings, 29:845-847 (1997).

Teitelman, et al., "Cells of mouse endocrine pancrease coexpress insulin, glucagon and the neuronal proteins tyrosine hydroxylase and neuropeptide Y, but not pancreatic polypeptide," Development, 118:1031-1039 (1993).

Torella, et al., "The cardiac stem cell: the adult mammalian heart harbours oct-4(pos) cardiac stem cells with very broad developmental potential", Circulation, 114(18):303 (2006).

Tropepe, et al., "Retinal stem cells in the adult mammalian eye" Science 287: 2032-2036 (2000).

Vacanti, et al. "Identification and initial characterization of spore-like cells in adult mammals", J Cell Biochem, 80: 455-460 (2001).

Vacanti, et al., "Tissue-engineered spinal cord", Transplantation Proceedings, 33:592-598 (2001).

Vinik, "Pancreatic Islet Cell Regeneration and Growth", Developmental Origin of Isolets During Emryogenisis, Plenurn Press, New York, 1-5 (1992).

Wakitani, et al., "Mesenchymal cell-based repair of large, full-thickness defects of articular cartilage", J. Bone Joint Surg. Am., 76(4):579-92 (1994).

Warejcka, et al., "A population of cells isolated from rate heart capable of differentiating into several mesodermal phenotypes" Journal of Surgical Research 62(2): 233-242 (1996).

Watt, "Epidermal stem cells: markers, patterning and the control of stem cell fate", Philos Trans R Soc Lond B Biol Sci., 353:831-837 (1998).

Weiss, et al., "Multipotent CNS stem cells are presnet in the adult mammalian spinal cord and ventricular neuroaxis" J. Neurosci., 16:7599-7609 (1996).

Weissman, "Translating stem and progenitor cell biology to the clinic; Barriers and opportunities" Science, 287: 1442-1446 (2000).

Yannas, et al., "Wound tissue can utilize a polymeric template to synthesize a functional extension of skin," Science, 215:174-176 (1982).

Zhao and Daley, "From fibroblasts to iPS cells: Induced pluripotency by defined factors", J. Cell. Biochem., 105(4):949-55 (2008).

Zuk, et al., "Human adipose tissue is a source of multipotent stem cells.", Molecular Biology of the Cell, 13:4279-4295 (2002).

Zulewski, et al., "Multipotential nestin-positive stem cells isolated from adult pancreatic Islets diffentiate ex vivo into pancreatic endocrine, exocrine, and hepatic phenotypes" Diabetes 50(3): 521-533 (2001).

Anversa, et al., "Life and death of cardiac stem cells a paradigm shift in cardiac biology", Circulation, 113(11:1451-3 (2006).

Colussi and Orlean, "The essential Schizosaccharomyces pombe gpil+ gene complements a bakers' yeast GPI anchoring mutant and is required for efficient cell separation", Yeast, 13:139-50 (1997).

Lemire, et al., "Oval cell proliferation and the origin of small hepatocytes in liver injury induced by D-galactosamine", Am J Pathol., 139(5):535-52 (1991).

Muraki, et al., "Assessment of viability and osteogenic ability of human mesenchymal stem cells after being stored in suspension for clinical transplantation", Tissue Eng., 12 (6):1711-9 (2006).

Pitt and Christian, "Heat resistance of xerophilic fungi based on microscopical assessment of spore survival", Appl. Microbiol., 20(5):682-5 (1970).

Shewan, et al., "mCD24, a glycoprotein transiently expressed by neurons, is an inhibitor of neurite outgrowth", J Neurosci., 16(8):2624-34 (1996).

Wolk, "Physiology and cytological chemistry blue-green algae", Bacteriol. Rev., 37(1):32-101 (1973).

\* cited by examiner

SUBPOPULATIONS OF SPORE-LIKE CELLS AND USES THEREOF

CROSS-REFERENCE TO RELATED APPLICATIONS

This application is a divisional of U.S. application Ser. No. 14/845,641, filed Sep. 4, 2015, now U.S. Pat. No. 9,663,765, which is a divisional of U.S. application Ser. No. 14/025,528, entitled "Subpopulations of Spore-Like Cells and Uses Thereof" by Martin P. Vacanti and Charles A. Vacanti, filed Sep. 12, 2013, now U.S. Pat. No. 9,145,545, which is a continuation of U.S. application Ser. No. 12/944,342, filed Nov. 11, 2010, now U.S. Pat. No. 8,551,775, issued Oct. 8, 2013, which claims benefit of and priority to U.S. Provisional Application Ser. No. 61/260,607 filed Nov. 12, 2009, all of which are herein incorporated in their entirety by reference.

FIELD OF THE INVENTION

The invention relates to the identification, isolation and uses of subpopulations of spore-like cells.

BACKGROUND OF THE INVENTION

The use of pluripotent cells has gained interest in medical research, particularly in the area of providing reagents for treating tissue damage either as a result of genetic defects, injuries, and/or disease processes. Ideally, cells that are capable of differentiating into the affected cell types could be transplanted into a subject in need thereof, where they would interact with the organ microenvironment and supply the necessary cell types to repair the injury. Embryonic stem (ES) cells are pluripotent cells derived from blastocysts that can be propagated indefinitely undifferentiated in vitro, can differentiate to all cell lineages in vivo, and can be induced to differentiate into most cell types in vitro (Martin, *Proc Natl Acad Sci USA.*, 78:7634-7638 (1981)). Although ES cells have been isolated from humans, their use in research as well as therapeutics is encumbered by ethical considerations (Frankel, *Science.* 287:1397 (2000)

There have been increasing efforts to isolate stem cells from non-embryonic tissues, including hematopoietic (U.S. Pat. No. 5,750,397), neural, Gage, *Science,* 287:1433-1438 (2000), gastrointestinal, Potten, *Philos Trans R Soc Lond B Biol Sci.* 353:821-830 (1998), epidermal, (Watt, *Philos Trans R Soc Lond B Biol Sci.*, 353:831-837 (1998), and mesenchymal stem cells (MSCs) (U.S. Pat. No. 5,736,396). Another population of cells, multipotent adult progenitor cells (MAPCs), has also been purified from bone marrow (Reyes et al., *Blood,* 98(9):2615-2625 (2001); Reyes & Vetfaillie, *Ann NY Acad Sci.,* 938:231-235 (2001)). These cells are capable of expansion in vitro for more than 100 population doublings without telomere shortening or the development of karyotypic abnormalities. MAPCs have also been shown to be able to differentiate under defined culture conditions into various mesenchymal cell types (e.g., osteoblasts, chondroblasts, adipocytes, and skeletal myoblasts), endothelium, neuroectoderm cells, and more recently, into hepatocytes (Schwartz et al., *Clin Invest,* 109:1291-1302 (2000)).

A challenge to the use of ES cells or other pluripotent cells for regenerative therapy in a subject is to control the growth and differentiation of the cells into the particular cell type required for treatment of a subject. As disclosed in Schuldiner et al., *Proc Natl Acad Sci USA,* 97:11307-11312 (2000), none of the eight growth factors used therein directed differentiation exclusively to one cell type. Thus, there continues to be a need for new approaches to generate populations of transplantable multi- and pluripotent cells suitable for a variety of applications, including treating injury and/or disease of various organs and/or tissues. Furthermore, sources of the multipotent or pluripotent cells are limited in that the cells must be harvested from living tissue.

U.S. Published Application Nos. 2004/0057942 and 2004/0033598 by Vacanti, et al., disclose small primitive cells which have an exceptionally high tolerance for oxygen deprivation. These cells, called "spore-like" cells, have been demonstrated to tolerate essentially complete oxygen deprivation for at least 24 hours (cells were viable despite oxygen deprivation for either four or 24 hours). Spore-like cells have a greater capacity to proliferate than terminally differentiated cells isolated from specialized tissues. Proliferative capacity is an important attribute because tissue engineering, cell therapies, and gene-based therapies are often hampered by physicians' inability to obtain sufficient numbers of cells to administer to a patient.

It is therefore an object of the present invention to provide subpopulations of spore-like cells expressing specific cell surface or gene expression markers.

It is also an object of this invention to provide a subpopulation of pluripotent spore-like cells, and a method for isolating a subpopulation of pluripotent spore-like cells.

SUMMARY OF THE INVENTION

Sub-populations of spore-like cells expressing specific cell surface receptors and/or gene expression markers have been identified. In one embodiment, the cells express at least one cell surface/gene expression marker such as Oct4, nanog, Zfp296, cripto, Gdf3, UtF1, Ecat1, Esg1, Sox2, Pax6, nestin, SCA-1, CD29, CD34, CD90, B1 integrin, cKit, SP-C, CC10, SF1, DAX1, and SCG10. In most embodiments the cells express a combination of markers. Also provided are subpopulations of spore-like cells which can be induced to differentiate into cells of endodermal, mesodermal or ectodermal origin. These subpopulations of spore-like cells, regardless of their tissue of origin, can be used to generate cells originating from all three germ layers. Methods for identifying and obtaining a subpopulation of spore-like cells are described. The methods include culturing isolated spore-like cells for a period of time sufficient for expression of cell surface and/or gene expression markers, and identifying the cell surface and/or gene express markers.

Methods for purifying a subpopulation of spore-like cells of interest from a population of spore-like cells are also described. In some embodiments, the methods includes (a) providing a population of spore-like cells; (b) identifying a subpopulation of the spore-like cells that express one or more markers such as Oct4, nanog, Zfp296, cripto, Gdf3, UtF1, Ecat1, Esg1, Sox2, Pax6, nestin, SCA-1, CD29, CD34, CD90, B1 integrin, cKit, SP-C, CC10, SF1, DAX1, and/or SCG10; and (c) purifying the sub-population. In some embodiments, the cells are isolated using antibodies specific for the cell surface markers.

Patients who have a disorder, such as a skin disorder, a tumor, or a disease, such as diabetes, can be treated for example, by administering a subpopulation of spore-like cells to the damaged region (e.g., the damaged region of the patient's skin, the area from which the tumor was ablated, or the pancreas). Systemic administration is also possible. The methods can be used to treat a patient who has a deficiency or disorder of functional cells in any of a wide variety of tissues, such as the retina, intestine, bladder, kidney, liver, lung, nervous system including spinal cord or brain, or endocrine system.

DETAILED DESCRIPTION OF THE INVENTION

I. Definitions

A pluripotent spore-like cell, as used herein, is a spore-like cell that has the ability to give rise to cells originating from all three germ layers: mesoderm, endoderm, and ectoderm.

The term "isolated", as used in the context of a spore-like cell, indicates that the cell exists apart from its native environment. An isolated cell can be completely isolated from other cell types, or be present in an increased amount in a population.

As used herein, an enriched spore-like cell population is a population of cells which have been isolated from other cells that exist in their native environment, so that the proportion of that cell in a mixture of cells is greater than would be found in its native environment or immediately following isolation.

As used herein, a "detectable label" refers to any moiety that can be added to a binding partner of interest, which allows for the detection of the binding partner.

II. Spore Like Cell Populations

Sources of Spore-Like Cells

Spore-like cells can be obtained from an animal donor such as an avian reptilian, amphibian, or mammalian animal. For example, mammalian spore-like cells can be isolated from a rodent, a rabbit, a cow, a pig, a horse, a goat, a sheep, a dog, a cat, a non-human primate, or a human. Spore-like cells can be obtained from a mature animal. Because spore-like cells tolerate oxygen deprivation better than differentiated cells, viable spore-like cells can also be isolated from deceased animals, including animals that have been deceased for 24 hours or more. Spore-like cells were isolated from chicken livers (avian class) purchased at a grocery store. At initial isolation a trypan blue dye exclusion test that showed very small viable (dye excluded) spore like cells. Three days following isolation large floating clusters of spore-like cells too numerous to count, could be seen (data not shown).

Within a given donor, spore-like cells can be obtained from a variety of sources. For example, spore-like cells can be obtained from bodily fluids (e.g., blood, saliva, or urine), and most, if not all, functional organs. Moreover, spore-like cells can be obtained from the patient who will be subsequently treated with those cells, from another person, or from an animal of a different species. Autologous, allogenic, and xenogeneic subpopulations spore-like cells can be obtained and used to treat patients or to grow tissues.

Figure 1:
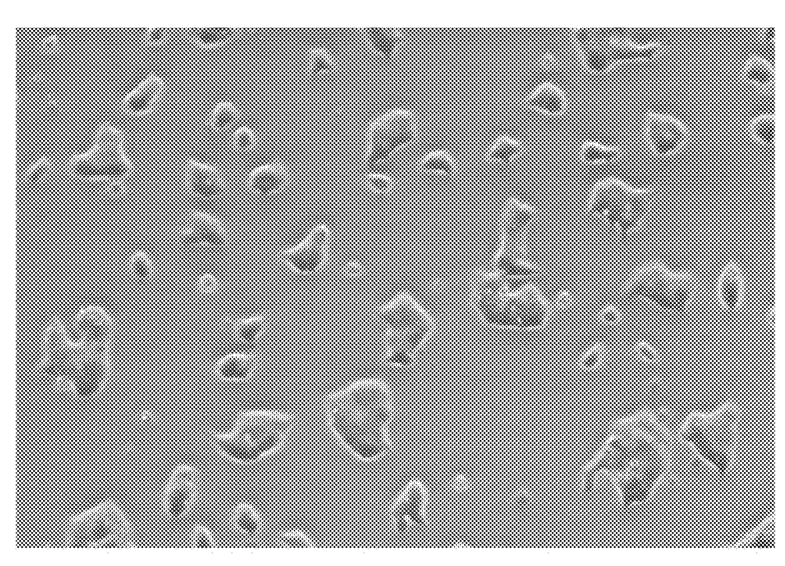
FIG. 1 shows spore-like cell isolated from an insulinoma (tumor from pancreas).

Spore-like cells can also be isolated from diseased tissue, for example, cancerous tissue (FIG. 1). Spore-like cells thus isolated have a significant regenerative potential under the right conditions.

Isolation of Spore-Like Cells

Methods for isolating spore-like cells are disclosed in U.S. Pat. Nos. 7,060,492, 7,575,921 and 7,560,275 to Vacanti, et al. Briefly, a tissue or blood sample is obtained from an animal. One of the easiest samples to obtain is a sample of whole blood. Those of ordinary skill in the art will appreciate that the isolation method may vary slightly depending on the type of tissue used as the starting material. For example, in the event the sample is a blood sample, it can be placed in a tube containing an anti-coagulant.

After collection, tissue samples, whether they are samples of bodily fluids or cell suspensions obtained from solid organs, are centrifuged for a time and at a speed sufficient to pellet the cells within the sample at the bottom of the centrifuge tube. The resulting pellet is re-suspended in a suitable medium such as DMEM/F-12 medium supplemented with glucose, transferrin, insulin, putricine, selenium, progesterone, epidermal growth factor (EGF) and basic fibroblast growth factor (bFGF).

The suspended cells are then transferred to a tissue culture vessel and incubated at or near 37° C. Initially, when the sample is a blood sample, the culture flasks contain primarily hematopoietic cells. However, after several days in culture, the red blood cells lyse so that the culture contains primarily, if not exclusively, spore-like cells. This is because the red blood cells have no nucleus; however, the spore-like cells stay alive under these conditions. When spore-like cells are isolated from solid tissues, the differentiated cells can be lysed by triturating the sample with a series of pipettes, each having a smaller bore diameter than the one before. For example, the last pipette used can have a bore diameter of approximately 15μ. After several additional days in culture, the spore-like cells multiply and can coalesce to form clusters (spheres) of cells. Over time, usually on the order of approximately 7 days, their number can increase greatly. Typically, more than 90% of the cells are viable according to Trypan blue exclusion studies when isolated as described above.

Those of ordinary skill in the art will recognize that trituration through reduced bore pipettes is not the only way to isolate spore-like cells from larger, differentiated cells. For example, a suspension containing spore-like cells and differentiated cells can be passed through a filter having pores of a particular size. The size of the pores within the filter (and, similarly, the diameter of the pipette used for trituration) can be varied, depending on how stringent one wishes the isolation procedure to be. Generally, the smaller the pores within the filter, or the smaller the diameter of the pipette used for trituration, the fewer the number of differentiated cells that will survive the isolation procedure. Other methods for isolating spore-like cells is freeze/thawing and size exclusion.

In some embodiments a method for isolating spore-like cells from blood/bone marrow while ensuring exclusion of types of cells/stem cells include: freezing anticoagulated whole blood down to −20 to −80° C. without adding any cyroprotectant agents, then thawing the frozen sample. The intracellular ice crystals formed during freezing will kill all other cells. The cells are them triturated in culture media and then cultured. The remaining cells that grow are spore-like cells. Other techniques to isolate spore-like cells from blood include oxygen deprivation for 24 hours. Blood or bone marrow samples are lyses with hypertonic solution to burst cells/stem cells. Not using serum nor feeder cells in your cultures selects for spore-like cells. These methods work well for blood as with other tissues.

Enrichment of Spore-Like Cell Subpopulations

A method for enriching and characterizing, identifying or analyzing the enriched subpopulation of spore-like cells is disclosed. The enriched subpopulations are identified using cell surface of gene expression markers expressed by the cells. The cells are cultured for a time period sufficient for specific marker expression, as demonstrated in the examples, and marker expression confirmed using techniques known to one of ordinary skill in the art. Enriched spore-like cell populations are positive for one or more specific cell markers, such as Oct4, nanog, Zfp296, cripto, Gdf3, UtF1, Ecat1, Esg1, Sox2, Pax6, nestin, SCA-1, CD29, CD34, CD90, B1 integrin, cKit, SP-C, CC10, SF1, DAX1, and SCG10. The enriched spore-like cell population can be used following detection of the markers of interest, the cells can be cultured further to encourage additional differentiation, or the cells expressing the markers can be further isolated from the enriched subpopulation.

Methods for isolating cells expressing a protein of interest for further propagation are known to one of ordinary skill in the art. For example, cells expressing a marker of interest can be isolated using commercially available ClonePix FL system (Gentix, UK) disclosed in U.S. Pat. No. 7,310,147, which works by imaging thousands of cells. Specific fluorescent probes are then used to detect and identify fluorescing colonies. Cells with the desired level of fluorescence (for example, the highest producers of a target protein) are then automatically collected (Mann, *Nature Methods*, i-ii, (2007)). Successive passage of spherical clusters of these cells results in a purer population of immature and more primitive stem cells. In other embodiments, cell surface or gene expression markers are used to isolate the subpopulations of spore-like cells of interest. In one embodiment for cell surface markers, the method includes (a) providing a population of spore-like cells isolated as described supra; (b) culturing the population of spore-like cells for a period of time sufficient to express the markers; (c) contacting the population of cells with a binding partner that is specific for a marker, and under conditions sufficient to allow binding of the binding partner to its target, if present, on each cell of the population of spore-like cell; and (d) isolating the marker-positive subpopulation.

In some embodiments, in step (c) discussed above, the cells are contacted with a first binding partner that is specific for a first marker, and a second binding partner that is specific for a second marker which is different from the first marker, under conditions sufficient to allow binding of each binding partner to its target, if present, on each cell of the population of spore-like cells; (d) selecting a first subpopulation of spore-like cells that are positive for the markers; (e) contacting the first subpopulation of spore-like cells with one or more additional binding partners that are specific for one or more additional cell surface markers under conditions sufficient to allow binding of each binding partner to its target, if present, on each cell of the population of cells; (f) removing from the first subpopulation of cells those cells that bind to at least one of the antibodies of step (e); and (g) collecting a second subpopulation of cells whereby a subpopulation of spore-like cells is isolated. In some embodiments, the binding partner is an antibody specific for the cell surface marker.

The isolation of the disclosed subpopulations can be performed using any methodology that can separate cells based on expression or lack of expression of the one or more specific markers including, but not limited to fluorescence-activated cell sorting (FACS). The markers are selected from the group consisting of Oct4, nanog, Zfp296, cripto, Gdf3, UtF1, Ecat1, Esg1, Sox2, Pax6, nestin, SCA-1, CD29, CD34, CD90, B1 integrin, cKit, SP-C, CC10, SF1, DAX1, SCG10, SCA-1, CD34, CD90, CKIT, B1 integrin.

The separation step can be performed in a stepwise manner as a series of steps or concurrently. For example, the presence or absence of each marker can be assessed individually, producing two subpopulations at each step based on whether the individual marker is present. Thereafter, the subpopulation of interest can be selected and further divided based on the presence or absence of the next marker.

Alternatively, the subpopulation can be generated by separating out only those cells that have a particular marker profile, wherein the phrase "marker profile" refers to a summary of the presence or absence of two or more markers. Each of these individual combinations of markers represents a different marker profile. As additional markers are added, the profiles become more complex and correspond to a smaller and smaller percentage of the original mixed population of cells. In some embodiments, antibodies specific for markers are employed for isolation and/or purification of subpopulations of spore-like cells that have marker profiles of interest, and it is understood that based on the marker profile of interest, the antibodies can be used to positively or negatively select fractions of a population, which in some embodiments are then further fractionated.

In some embodiments, the binding partners are labeled with a detectable label. Different binding partners which bind to different markers can be labeled with different detectable labels or can employ the same detectable label. A variety of detectable labels are known to the skilled artisan, as are methods for conjugating the detectable labels to biomolecules such as antibodies and fragments and/or derivatives thereof. Representative detectable moieties include, but are not limited to, covalently attached chromophores, fluorescent moieties, enzymes, antigens, groups with specific reactivity, chemiluminescent moieties, and electrochemically detectable moieties, etc. In some embodiments, the binding partners are biotinylated. In some embodiments, the biotinylated binding partners (the first binding partner) which bind to markers on the cell surface are detected using a second binding partner comprising an avidin or streptavidin group that is conjugated to a fluorescent label including, but not limited to, Cy3, Cy5, and Cy7. In some embodiments, the binding partner is directly labeled with a fluorescent label such as Cy3, Cy5, or Cy7. In some embodiments, the binding partner is directly labeled with a fluorescent label and cells that bind to the antibody are separated by fluorescence-activated cell sorting. Additional detection strategies are known to the skilled artisan.

III. Applications of Subpopulations of Spore-Like Cells

Cell Culture and Genetic Manipulation

The cells disclosed herein can be administered directly to a patient, induced to differentiate into cells of any of endodermal, ectodermal or mesodermal origin prior to administration, or, they can be made to express particular factors following genetic manipulation. For example, the subpopulation of spore-like cells can be made to express hormones, such as insulin, by transfecting them with gene constructs that include sequences that encode these factors.

Differentiation of Subpopulations of Spore-Like Cells

The subpopulation of spore-like cells, regardless of their tissue of origin, can be induced to different into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells (e.g., alpha cells, delta cells, PP cells, and beta cells), blood cells (e.g., leukocytes, erythrocytes, macrophages, and lymphocytes), retinal cells (and other cells involved in sensory perception, such as those that form hair cells in the ear or taste buds on the tongue), nervous tissue including brain and nerves, and fibroblasts.

The subpopulations of spore-like cells can be induced to differentiate in a variety of ways. Marker positive spore-like cells can differentiate when they establish contact with a tissue within a patient's body or are sufficiently close to a tissue to be influenced by substances (e.g., growth factors, enzymes, or hormones) released from the tissue. Differentiation of the cells is influenced by virtue of signals the cell receives from the surrounding tissue. Such signaling occurs, for example, when a receptor on the surface of the cell is bound and transduces a signal from a molecule such as a growth factor, enzyme, or hormone that is released by a tissue within the patient. Alternatively, or in addition, cells disclosed herein can be induced to differentiate by adding a substance (e.g., a growth factor, enzyme, hormone, or other signaling molecule) to the cell's environment. For example, a substance can be added to a culture dish containing a subpopulation of spore-like cells, to a mesh or other substrate suitable for applying cells to a tissue, or to a tissue within a patient's body. When a substance that induces cells to differentiate is administered, either systemically or locally, it can be administered according to pharmaceutically accepted methods. For example, proteins, polypeptides, or oligonucleotides can be administered in a physiologically compatible buffer, with or without a carrier or excipient. Thus, the subpopulations of spore-like cells can differentiate either in culture or in a patient's body, and may do so following contact with a solid support or exposure to substances that are either naturally expressed, exogenously administered, or expressed as a result of genetic manipulation.

In one embodiment, the spore-like cell population is induced to differentiate into cells of ectodermal origin by exposing the cells to an "ectodermal differentiating" media. In another embodiment the spore-like cells population is induced to differentiate into cells of mesodermal origin by exposing the cells to "mesodermal differentiating media". In still another embodiment, the spore-like cell population is induced to differentiate into cells of endodermal origin by exposing the cells to "endodermal media". Components of "endodermal", "mesodermal" and "ectodermal" media are known to one of ordinary skill in the art. Known cell surface markers can be used to verify that the cells are indeed differentiating into cells of the lineage of the corresponding cell culture medium. The most commonly accepted markers to confirm differentiation of the three germ layers are the expression of alpha fetal protein for endodermal cells, alpha smooth muscle actin for mesoderm, and Beta-III tubulin for ectoderm, all of which are normally expressed very early in the development of these tissues.

Regardless of the stimulus for differentiation, the subpopulation of spore-like cells that have differentiated, or that will do so, sufficiently to aid in the maintenance or repair of tissue, can be administered to a patient (e.g., at the site of a burn or other traumatized area of skin, a bone fracture, a torn ligament, an atrophied muscle, a malfunctioning gland, or an area adversely affected by a neurodegenerative process or autoimmune response).

Tumor Spore-Like Cells
(i) Vaccine Treatment

Subpopulations of spore-like cells obtained may be very useful research tools and have a potential for therapy, for example, spore-like cells isolated from a tumor from pancreas may be used with dendritic antigen presenting cells as a continuous cell mediated vaccine.

Current experimental dendritic vaccines work for a brief period but eventually fail, most likely because they are derived from mature tumor cells. If the tumor cells change genetically, then the vaccine may become useless, similar to what occurs with viral influenza vaccines from year to year. Having a powerful evolving tumor stem cell should make for a more effective vaccine. Tumor-derived spore-like cell populations may be cultures and used to stimulate cells of the immune system to attack and potentially treat tumors or malignancies, as demonstrated for example in Liau et al., *J. of Neuro.* 90 (6):1115-24 (1999). Liau, et al., (1999) demonstrated that a special type of brain tumor (intra cranial glioma) may be treated by actually isolating these brain tumor cells and stimulating a special type of immune cell that can be derived from a patient called a dendritic cell, that actually then processes the antigens produced by the tumor cells and consequently stimulates the rest of the immune system to attack the actual brain tumor resulting in regression or disappearance of the tumor. This attack is mediated through the production of cytokines produced by such immune cells as T-8, T-4 as well as B cells and natural killer cells. This particular approach has shown therapeutic benefit in both animals and early human trials in treating brain tumors. One of the main limitations of this technology is that although an effective vaccine can be made against a particular type of tumor cell, over time tumors mutate and consequently new tumors may arise that will not be responsive to the initial vaccine. Thus the tumor derived spore-like cells that will express a greater variety of antigens and can continuously be kept in culture can be used in stead of tumor cells. As these spore like cells express antigens and mutate, updated vaccines can be synthesized and used to treat tumor recurrences in the patient. We have noted the presence of spore-like cells in a special type of tumor called an insulinoma. There is no reason to expect that spore-like cells can not be isolated from all tumor types. One potential advantage of using tumor derived spore-like cells to stimulate a vaccine is the fact that since spore-like cells very primitive they have the full potential to express and differentiate into multiple varieties of tumor cells and express multiple antigens. In other words, if a more fundamental tumor cell is used to make a vaccine, then the variety of the immune response to a cell that has a larger potential to make different types of tumor antigens, would have an end result in a more powerful vaccine due to normal mutations that occur in tumors. Additionally spore-like cells maybe isolated from the blood, bone marrow and thymus with the capacity to differentiate into all cell types of the immune system including natural killer cells, T-4 and T-8 cells, and B or antibody producing cells. Furthermore, dendrocytes (antigen presenting cells) may evolve from spore-like cells. This would allow the possible in vitro stimulation of the immune system not only by various types of tumor cells, but also by micro organisms such as viruses, HIV, and bacteria such as anthrax. This may provide a mechanism to create new vaccines to tumors, and infectious diseases such as HIV and anthrax. Additionally spore-like cells derived from a tumor by a biopsy maybe cultured in vitro and different therapeutic agents can be used to test the effect on the in vitro malignant spore-like cells thus predicating the patient response whether it be a chemotherapeutic agent, vaccine or radiation.

Just like bacteria are isolated from sick patients with culture and sensitivities done to choose effective antibiotic treatment, so to will the isolation of tumor spore like cells from a biopsy sample make tumor culture and chemotherapy sensitivity testing possible. Additionally tumor spore like cells isolated from a patient will be suited for use in the evolving field of molecular diagnostics and proteonomics, to profile the patient's tumor for needed diagnosis and therapeutic intervention.

(ii) DNA Repair in Tumor Cells

DNA in living cells is constantly exposed to damaging agents such as radiation, carcinogens and oxidation. It has been known that damaged DNA is associated with malignant transformation of cells. Consequently cells are protected from becoming malignant by the presence of DNA repair genes. For instance, if someone has a genetic predisposition to a particular type of cancer, in some cases a defect in this DNA repair system can be demonstrated. One example is the hereditary non-polyposis colon cancer syndrome. This consists of a defect in DNA repair that is expressed as familial cancer of the colon. A nucleotide mismatch can result in cancer. Normal DNA repair genes would correct this mismatch and consequently tumor formation is averted. Recent stem cell research has shown neuronal stem cells to possess the capability of following and tracking down a migrating glioma (a special type of brain tumor) cells. Because of this tumor tracking phenomena, neural stem cells have had genes inserted into them for chemicals such as interferon-gamma, tumor necrosis factor and interleukin 12. Upon implantation these unique stem cells were able to track down the brain tumor cells and damage them by secreting the anti-tumor chemical. Additionally recent literature has demonstrated that adult stem cells have the capacity to fuse with normal cells when placed in the body. Disclosure relevant to DNA repair as discussed above can be found for example in Ourednik, et al., *Nature Biotechnol.*, 20 (11): 1103-1110 (2002); Stewart, et al., *Bioessays*, 24 (8): 708-13 (2002); Ehtesham, et al., *Cancer Therapy*, 9 (11): 925-934 (2002); Ehtesham, et al., *Cancer Reserves*, 62 (20): 5657-63 (2002); Ferguson, et al., *Oncogene* 20(40): 5572-9 (2001).

The spore-like cells populations disclosed herein can therefore be used to treat tumors using the unique properties of seeking out malignant cells by tracking, fusion, and DNA repair. In vitro spore-like cells have been observed to cluster and fuse with normal cells that are grown in culture with the spore-like cell. Spore-like cells can easily be isolated from non-prepared anticoagulated frozen blood and expanded in culture. As opposed to neural stem cells these spore-like cells are easily derived, especially from the blood and rapidly increase in numbers when incubated. Additionally, they are small consequently having a greater opportunity to fuse with tumor cells because of their great numbers, small size and very simple structure. Previous descriptions show essentially a very small simple structure or packets of membrane bound DNA. All cells have natural DNA repair systems. An example would be endonucleases that can cut out damaged, defective DNA and then replace these damaged DNA segments with normal DNA using DNA polymerases. As cells age, their DNA repair systems fail with consequent malignant transformation. Most therapeutic modalities for cancer focus on surgical removal of the tumor and the use of tumor cell killing mechanisms such as chemotherapy, radiation, or immunotherapy. These approaches are associated with significant morbidity and are not always effective. There are no approaches of using DNA repair to convert a tumor cell into a normal cell, even though these repair systems are known to exist, and their failure is involved in the causing of cancer. The infusion of billions of spore like cells derived from the patient's own blood, with fresh DNA repair systems that can seek out and track down tumor cells would have the capacity to fuse with the tumor cells and donate their DNA repair systems to the defective tumor cells. They may also exert a repair effect on the tumor cells by secreting agents with trophic effects. These spore-like cells could be directly infused into the tumor or given by IV or IP routes. Since this would be an augmentation of natural DNA repair systems known to exist, side effects would be minimal compared to more traditional cell suicidal approaches such as chemotherapy. Essentially an unlimited number of spore-like cells could be generated from the patient's own blood to accomplish this task.

Additionally, gene insertion technology can be used to insert nucleotide sequences into spore like cells that express anti-tumor substances, such as interferon gamma and tumor necrosis factor. Once infused, these genetically engineered spore-like cells would track down and fuse with the tumor cells delivering the interferon, or TNF directly to the tumor with therapeutic effect. This represents an improvement in prior art, because spore-like cell populations can be expanded in vitro to supply an inexhaustible amount of simple cell structures that can track down, fuse and consequently repair the damaged DNA found in tumor cells. Prior art has demonstrated that neural stem cells possess these properties, but harvesting neural stem cells from a patient maybe associated with many risks. This treatment approach may have uses for cancers of the breast, lung, brain, and prostrate as well as other organs.

(iii) Reversal of Degenerative Diseases

Gene based therapeutics or gene insertion technology involves effective delivery of specific nucleotide sequences or genes will result in a clinical improvement because of the production of a needed protein produced by the specific gene. Potential uses include treatment modalities for cancer, vaccines, genetic and metabolic disorders, and other areas including viral infections, cardiovascular disease and other organ disease states. One of the major limitations of gene based therapeutics has been finding an adequate and effective delivery system. Much work has been done in regards to gene insertion and adenoviral vectors with the consequent infection of the patient resulting in the expression of the needed protein because of insertion of the needed therapeutic gene. Problems have included ineffective gene insertion into the desired host cells as well as hazardous effects of the viral vector actually infecting the host. As demonstrated in the example, spore-like cell populations can be easily isolated from the patient including blood expanded in vitro; the spore-like cells can be safely returned to the patient by various routes such as IV, intraperitoneal or subcutaneously to name a few. Genes encoding proteins such as Factor 8 (for treatment of hemophilia) can be inserted in an in vitro environment with expansion of the spore-like cell population with the new therapeutic gene and product using techniques such as those disclosed in Vacanti, et al., *Transplantation Proceedings*, 33:592-598 (2001). Additional evidence of potential use includes the expression of Brdu, indicating active nucleic acids synthesis. This method may also allow the actual in vitro production of needed therapeutic proteins such as Factor 8 utilizing the spore-like cell population in recombinant techniques with the consequent production of a therapeutic protein. Ideally, a permanent in vivo effect may be possible. For examples, blood spore like cell populations can be isolated from a patient with hemophilia or Tay Sach's disease, a gene inserted in vitro, then the corrected cells could be safely implanted back into the patient with proliferating cells with the potential to correct the enzyme deficiency and cure the disease. Any known gene enzyme deficiency resulting in a disease may be amenable to treatment using this approach. Potentially treatable genetic diseases include Huntington's Disease, muscular dystrophy, familial hypercholesterolemia, cystic fibrosis, phenylketonuria, hemachromatosis, sickle cell anemia, and glycogen storage disease to name a few. With the mapping of the human genome, eventually most the genetic mutations resulting in disease will be worked out opening up the opportunity for treatment with appropriate gene insertion technology. Autologous derived spore like cell populations may provide the needed vehicle of delivery of these corrected genes. The properties of their small size and exuberant ability to divide and to allow the insertion of therapeutic nucleic acids sequences with expression, indicates that this is a reasonable application. The gene insertion may occur into the spore-like cell in vitro with just naked DNA alone which includes the needed gene sequence. This would avert any sort of potential hazards involving the use of viral vectors such as the adenoviral technique. Using this mode of gene insertion may provide additional modalities of therapy such as inserting nucleic acid sequences to make therapeutic agents such as a tumor suppressor protein, or an angiogenesis inhibitor to stop tumors from growing. Another gene which could be inserted into the spore-like cell populations includes a vasoactive gene such as VEGF to treat ischemic heart disease thus avoiding the need for bypass heart surgery. The CFRT gene which will make a protein to treat cystic fibrosis may be expressed by spore-like cells that have traveled to the lung through the circulation or have been injected into the lung through the bronchi with consequent engraftment, and differentiation in the lung tissue with generation of a needed gene product to help treat the symptoms of cystic fibrosis.

If bulk production of a needed product is desired the spore like cell could be implanted with biodegradable scaffolding material, hydrogels, or a naturally derived matrix such as we have isolated from frozen blood and other tissues such as heart, lung and CSF. A prior limitation of gene insertion therapy has been over time the amount of product dwindles probably due to dissipation of corrected cells into the body and eventual disappearance. The production of a tissue construct using the spore-like cell population with inserted gene nucleotides on a natural or bio-degradable scaffolding would be a way to overcome this limitation.

Structures and Formulations for Administration of Cells

The cell populations can be administered to a patient by way of a composition that includes a population of spore-like cells alone or on or in a carrier or support structure. In many embodiments, no carrier will be required. The spore-like cells will be administered by injection onto or into the site where the cells are required. In these cases, the cells will typically have been washed to remove cell culture media and will be suspended in a physiological buffer.

In other embodiments, the cells will be provided with or incorporated onto or into a support structure. Support structures may be meshes, solid supports, tubes, porous structures, and/or a hydrogel. The support structures may be biodegradable or non-biodegradable, in whole or in part. The support may be formed of a natural or synthetic polymer, metal such as titanium, bone or hydroxyapatite, or a ceramic. Natural polymers include collagen, hyaluronic acid, polysaccharides, and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters.

Solid Supports

The support structure may be a loose woven or non-woven mesh, where the cells are seeded in and onto the mesh. The structure may include solid structural supports. The support may be a tube, for example, a neural tube for regrowth of neural axons. The support may be a stent or valve. The support may be a joint prosthetic such as a knee or hip, or part thereof, that has a porous interface allowing ingrowth of cells and/or seeding of cells into the porous structure.

The support structure may be a permeable structure having pore-like cavities or interstices that shape and support the hydrogel-cell mixture. For example, the support structure can be a porous polymer mesh, a natural or synthetic sponge, or a support structure formed of metal or a material such as bone or hydroxyapatite. The porosity of the support structure should be such that nutrients can diffuse into the structure, thereby effectively reaching the cells inside, and waste products produced by the cells can diffuse out of the structure The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape. The support can be shaped either before or after the support structure is seeded with cells or is filled with a hydrogel-cell mixture, as described below.

Additional factors, such as growth factors, other factors that induce differentiation or dedifferentiation, secretion products, immunomodulators, anti-inflammatory agents, regression factors, biologically active compounds that promote innervation or enhance the lymphatic network, and drugs, can be incorporated into the polymer support structure.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape. Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Many other types of support structures are also possible. For example, the support structure can be formed from sponges, foams, corals, or biocompatible inorganic structures having internal pores, or mesh sheets of interwoven polymer fibers. These support structures can be prepared using known methods.

Hydrogels

In another embodiment, the cells are mixed with a hydrogel to form a cell-hydrogel mixture. This cell-hydrogel mixture can be applied directly to a tissue that has been damaged. For example, as described in U.S. Pat. No. 5,944,754 a hydrogel-cell mixture can simply be brushed, dripped, or sprayed onto a desired surface or poured or otherwise made to fill a desired cavity or device. The hydrogel provides a thin matrix or scaffold within which the cells adhere and grow. These methods of administration may be especially well suited when the tissue associated with a patient's disorder has an irregular shape or when the cells are applied at a distant site (e.g., when spore-like cells are placed beneath the renal capsule to treat diabetes).

Alternatively, the hydrogel-cell mixture can be introduced into a permeable, biocompatible support structure so that the mixture essentially fills the support structure and, as it solidifies, assumes the support structure's shape. Thus, the support structure can guide the development and shape of the tissue that matures from spore-like cells, or their progeny, that are placed within it. As described further below, the support structure can be provided to a patient either before or after being filled with the hydrogel-cell mixture. For example, the support structure can be placed within a tissue (e.g., a damaged area of the skin, the liver, or the skeletal system) and subsequently filled with the hydrogel-cell composition using a syringe, catheter, or other suitable device. When desirable, the shape of the support structure can be made to conform to the shape of the damaged tissue. In the following subsections, suitable support structures, hydrogels, and delivery methods are described.

The hydrogels should be biocompatible, biodegradable, capable of sustaining living cells, and, preferably, capable of solidifying rapidly in vivo (e.g., in about five minutes after being delivered to the support structure). Large numbers of cells can be distributed evenly within a hydrogel. A hydrogel can normally support approximately $5 \times 10^6$ cells/ml. Hydrogels also enable diffusion so that nutrients reach the cells and waste products can be carried away.

A variety of different hydrogels can be used. These include, but are not limited to: (1) temperature dependent hydrogels that solidify or set at body temperature (e.g., PLURONICS™); (2) hydrogels cross-linked by ions (e.g., sodium alginate); (3) hydrogels set by exposure to either visible or ultraviolet light, (e.g., polyethylene glycol polylactic acid copolymers with acrylate end groups); and (4) hydrogels that are set or solidified upon a change in pH (e.g., TETRONICS™). Methods for the synthesis of the other polymers described above are known to those of ordinary skill in the art. See, for example Concise Encyclopedia of Polymer Science and Engineering, J. I. Kroschwitz, Ed., John Wiley and Sons, New York, N.Y., 1990. Many polymers, such as poly(acrylic acid), alginates, and PLURONICS™ are commercially available.

Ionic polysaccharides, such as alginates or chitosan, can be used to suspend living cells, including spore-like cells and their progeny. These hydrogels can be produced by cross-linking the anionic salt of alginic acid, a carbohydrate polymer isolated from seaweed, with ions, such as calcium cations. The strength of the hydrogel increases with either increasing concentrations of calcium ions or alginate. U.S. Pat. No. 4,352,883 describes the ionic cross-linking of alginate with divalent cations, in water, at room temperature, to form a hydrogel matrix.

The subpopulations of spore-like cells are mixed with an alginate solution. The solution is delivered to an already implanted support structure, which then solidifies in a short time due to the presence of physiological concentrations of calcium ions in vivo. Alternatively, the solution is delivered to the support structure prior to implantation and solidified in an external solution containing calcium ions.

In general, these polymers are at least partially soluble in aqueous solutions (e.g., water, aqueous alcohol solutions that have charged side groups or monovalent ionic salts thereof). There are many examples of polymers with acidic side groups that can be reacted with cations (e.g., poly (phosphazenes), poly(acrylic acids), and poly(methacrylic acids)). Example s of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10 and 18.5 kDa. Smaller polymers result in gels of higher density with smaller pores.

Temperature-dependent, or thermosensitive, hydrogels can also be used. These hydrogels have so-called "reverse gelation" properties, i.e., they are liquids at or below room temperature, and gel when warmed to higher temperatures (e.g., body temperature). Thus, these hydrogels can be easily applied at or below room temperature as a liquid and automatically form a semi-solid gel when warmed to body temperature. As a result, these gels are especially useful when the support structure is first implanted into a patient, and then filled with the hydrogel-cell composition. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing spore-like cells and their progeny to survive and be nourished.

U.S. Pat. No. 4,188,373 describes using PLURONIC™ polyols in aqueous compositions to provide thermal gelling aqueous systems. U.S. Pat. Nos. 4,474,751, 4,474,752, 4,474,753, and 4,478,822 describe drug delivery systems that utilize thermosetting polyoxyalkylene gels. With these systems, both the gel transition temperature and/or the rigidity of the gel can be modified by adjustment of the pH and/or the ionic strength, as well as by the concentration of the polymer.

Other suitable hydrogels are pH-dependent. These hydrogels are liquids at, below, or above specific pH values, and gel when exposed to specific pHs, for example, 7.35 to 7.45, the normal pH range of extracellular fluids within the human body. Thus, these hydrogels can be easily delivered to an implanted support structure as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

Other hydrogels that can be used to administer spore-like cells or their progeny are solidified by either visible or ultraviolet light. These hydrogels are made of macromers including a water soluble region, a biodegradable region, and at least two polymerizable regions (see, e.g., U.S. Pat. No. 5,410,016). For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, for example, long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Hydrogels may be administered by injection or catheter, or at the time of implantation of other support structures. Crosslinking may occur prior to, during, or after administration.

Unless defined otherwise, all technical and scientific terms used herein have the same meanings as commonly understood by one of skill in the art to which the disclosed invention belongs. Publications cited herein and the materials for which they are cited are specifically incorporated by reference.

EXAMPLES

Using the methods described in the patent application, populations of spore like cells were isolated from bone marrow as well as several tissues representing endoderm, mesoderm and ectoderm. Immediately after isolation, the cells were placed in a media referred to as "basic media" composed of DMEM/F12 with antibiotics B27, FGF and EGF. The cells were maintained in the basic media for several weeks during which time sequential studies were performed to identify markers expressed by these cells. Markers were identified using both gene expression analysis and immunohistochemistry to identification of protein expression.

Spore-like cells acquired from tissues representative of endoderm, mesoderm and ectoderm were analyzed for expression of markers associated with embryonic stem cells, while exposed to the "basic media". Populations of spore-like cells procured from endodermal tissue (lung and liver), mesodermal tissue (muscle) and ectodermal tissue (spinal cord and adrenal gland), all expressed the same panel of genetic and protein markers as the bone marrow acquired spore-like cells, as well as absence of the same markers as bone marrow derived spore-like cells while maintained in the "basic media".

Cells were then exposed to one of three differentiating media: Endoderm differentatiating media, Mesoderm differentatiating media, and Ectoderm differentatiating media. The composition of the media is as follows:

Endoderm differentatiating media: Hepatocyte culture media ascorbic acid, BSA-FAF, hydrocortisone, transferrin, insulin, hEGF, genomyosin, plus 10% fetal bovine serum.

Mesoderm differentatiating media: DMEM plus 20% fetal bovine serum

Ectoderm differentatiating media: 10% fetal bovine serum added to the basic media composed of DMEM/F12 plus B27, BEDA FGF, EGF.

When the spore-like cell populations, including disaggregated clusters acquired from bone marrow and from each of the representative tissues, were exposed to each of the "differentatiating medias" supplemented as described above, the cells differentiated into cells representative of either endoderm, mesoderm or ectoderm, as a function of the media used, as determined by the expression of known protein and genetic markers, i.e., when an Endoderm differentiating media was used, the cells expressed the following protein markers consistent with endodermal tissue: cytokeratin 18, albumin and alpha fetal protein. The genetic marker, GATA4 was also expressed.

When a Mesoderm differentiating media was used, the cells expressed the following protein markers consistent with Mesodermal tissue: Myosin, desmin, alpha smooth muscle actin. The genetic marker burachyury was also expressed.

When an Ectoderm differentatiating media was used, the cells expressed the following protein markers consistent with Ectodermal tissue: Nestin, Map2 Beta-III tubulin (both of which are markers of neurons), 04 (a marker of oligodendrocytes), GFAPs (a marker of glial cells). Expression of Map2 was also verified by gene expression analysis.

As would be understood by one of ordinary skill in the art, the most commonly accepted markers to confirm differentiation of the three germ layers are the expression of alpha fetal protein for endoderm, alpha smooth muscle actin for mesoderm, and Beta-III tubulin for ectoderm, all of which are normally expressed very early in the development of these tissues. In addition, the genetic markers map2, burachyury and gata4 are expressed quite early in the germ layer formation of the embryo.

Results (i) Bone Marrow Derived Spore-Like Cells:

Spore-like cell populations isolated from the bone marrow generated multi cellular clusters within several days. Individual cells, either contained within the clusters, or alone expressing the following genetic markers, all of which have been associated with embryonic stem cells: Oct4, Nanog, Dax1, Fgf4, Zfp296, Cripto, Gdf3, Utf1, Cdx2, Ecat1, Esg1, Sox2 and Pax6, cMyc (a proliferative gene), Fgf5, Olig2 and Pdgfrl2. Also the marker nestin (a marker generally associated with neural stem cells) was noted.

Oct4 is a POU transcription factor and nanog is an NK-2 class homebox transcription factor, both of which have been associated with the maintenance of the undifferentiated state and pluripotency in embryonic stem cells. (Pan, et al., *Cell Res.*, 12:321-329 (2002); Clark, et al., *Stem Cells*, 22: 169-179 (2004); Niwa, *Development*, 134:635-646 (2007)). Cripto (teratocarcinoma-derived growth factor 1), a marker expressed early in the inner cell mass, is a multifunctional cell surface protein with important roles in vertebrate embryogenesis (Strizzi, *Oncogene*, 24:5731-5741 (2005)). GDF3 is a member of the TGFβ super family of ligands that is specifically expressed in the pluripotent state (Levine, *Development*, 133:209-16 (2005)). Undifferentiated embryonic transcription factor (Utf1) was first identified as a transcription co-factor that is expressed in mouse embryonic stem cells in a stem-cell specific manner. Utf1 is presumed marker for pluripotency (Niwa, *Cell Structure and Function*, 26(3):137-148 (2001)). Embryonic stem cell associated transcript 1 (Ecat1) is an embryonic stem cell-associated trans gene. Embryonic stem cell-specific gene (Esg1) which encodes a KH-domain containing protein, is expressed in pluripotent cells, including ES cells, embryonic germ cells, and multipotent germ line stem cells (Kanatsu-Shinohara, *Cell*, 1001-1012 (2004)). SRY (sex determining region Y)-box 2, also known as Sox2 and Pax6 are markers associated with both ES cells and neural stem cells. Sox2 is one of the key transcription factors required in induced pluripotent stem cells (Zhao, *J. Cell. Biochem.* 105(4): 949-55 (2008)). Nestin is a class VI intermediate filament protein expressed predominantly in stem cells from the central nervous system (Frederisken, et al., *J. Neurosci.*, 8:1144-51 (1988)). Thus, the spore-like cells obtained from the bone marrow express markers indicative of pluripotency.

The cells also expressed the following protein markers associated with embryonic stem cells: C-kit and Sca1 (surface markers) and E-cadherin as demonstrated by immunohistochemistry.

Of note is the fact that the spore-like cells isolated from the bone marrow stained negative for the following embryonic stem cell markers: Dax1, fibroblast growth factor 4 (Fgf4), caudal type homeobox transcription factor 2 (Cdx2), Neo and Eras (a tumor formation gene of ES), and Rex 1. The cells also stained negative for P75 a neural crest stem cell marker. Nor did they express the protein markers: Cd45 Cd31 or Cd34 (endothelial and hematopoietic stem cell markers).

(ii) Muscle

Spore-like cells obtained from muscle initially expressed the same embryonic stem cell markers observed with the spore-like cells obtained from the bone marrow, i.e., the cells expressed Oct4, Dax1, Fgf4, Zfp296, Cripto Gdf3, Utf1, Cdx2, Ecat1, Esg1, Sox2 and Pax6, cMyc, Fgf5, Olig2, Pdgfrl2.

The muscle-derived spore-like cells, like the bone-marrow derived spore-like cells, stained negative for Dax1, Fgf4, Cdx2, Neo and Eras, Rex 1 (embryonic stem cell markers), P75 (neural crest marker, Cd45 or Cd31 (endothelial and hematopoietic stem cell markers).

The spore-like cells isolated from muscle were studied after they formed multi cellular clusters (in the form of spheres).

The spheres started to form as early as a few days, but were not tested for markers for at least 3 weeks after initial isolation. The spheres ultimately grew to sizes of more than 300 microns in diameter. Spheres formed from muscle spore-like cells stained positive for the following markers: ckit, a cell surface marker indicating a stem cell, not necessarily an embryonic stem cell (ESC)). Almost 50% of the cells in the spheres were positive at 3 weeks, however, at 90 days, only 1-5% were positive (this indicates that they were losing their "stem cellness", as they matured).

Cells shed from myospheres were also analyzed. These are cells that are derived and shed from the myospheres as they grow and mature. Antibodies for Stem cell antigen 1 (Sca-1), CD31, and CD45 were all directly conjugated to PE. Antibodies for CD29, CD34, and CD90 were all directly conjugated to FITC. Cells in the spheres were positive for the following markers: SCA-1, CD29, CD34, CD90 and B1 integrin, while they were negative for CD31, CD45, which are hematopoietic and endothelial cell markers of more mature cells.

Marker expression changed with the passage of time. As cells that were shed from the spheres attached, they lost the immature marker CD90 first, then started to lose Sca-1. Also, myosphere cells did not express the mature cell marker, MyoD and expressed very little or no Pax7 and Myf5.

However when these myospheres were plated, adherent cells matured to expressed Pax7, MyoD, and Desmin and after adding in differentiation media fused to form multinucleated myotubes. Myosphere cells plated in adipogenic and osteogenic media differentiated into fat and bone. When myosphere derived cells were labeled with GFP and then injected into muscle, they generated GFP labeled muscle fibers. Cells generated through the formation of myospheres are multipotent stem cells since they do not yet express myogenic markers such as: Pax7, Myf5, and MyoD, yet they express these markers as they mature, and are able to form multi-nucleated myotubes, adipogenic and osteogenic cells, and can regenerate injured muscle in vivo. The staining for MyoD (nuclear), Desmin (cytoplasmic) and Sca 1 (surface) was shown in yellow-red. The staining for Pax7 (nuclear) was shown in green. The findings were confirmed with reverse transcriptase PCR in that myospheres are pre-myogenic, and they do not express Pax7, Myf5, or MyoD. While cells that shed from the myospheres attached and then matured to express Pax7, Myf5, and MyoD.

(iii) Lung

A similar time-dependent expression of markers was observed with spore-like cells isolated from the lung. Spore-like cells isolated from the lung initially express cKit, and then Nestin.

Later, cells shed from the spheres expressed SP-C, a marker for type II epithelial cells in alveoli (gene expression and protein analysis), and CC10 for Clara cells (gene expression and protein analysis).

(iv) Adrenal Gland

Adrenal gland expresses very early stem cell markers then matures to express markers of chromaffin cells and cell that make catecholamines. When initially isolated, spore-like cells obtained from the adrenal gland, like the cells from the bone marrow, expressed Oct4, Dax1, Fgf4, Zfp296, Cripto Gdf3, Utf1, Cdx2, Ecat1, Esg1, Sox2 and Pax6, cMyc, Fgf5, Olig2, Pdgfrl2.

The adrenal gland-derived spore-like cells similarly stained negative for Dax1, Fgf4, Cdx2, Neo and Eras, Rex 1 (embryonic stem cell markers), P75 (neural crest marker, Cd45 or Cd31 (endothelial and hematopoietic stem cell markers).

In time the mature cell markers were expressed: SF1, a steroidogenetic marker of the adrenal cortex, DAX1, SCG10 progenitor, cromaffin.

(v) Brain and Peripheral Nervous System

Brain and peripheral nervous system include: brain, spinal cord and peripheral nerve. In these tissues we have identified embryonic markers Sca-1, and Oct-4. They mature to show nestin, other neuro markers and a marker for Schwann cells in peripheral nerve.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a sub-population of spore-like cells expressing one or more markers selected from the group consisting of zinc finger protein 296 (Zfp296), cryptic family protein 1B (crypto), growth differentiation factor-3 (Gdf3), undifferentiated embryonic cell transcription factor 1 (UtF1), embryonic stem cell associated transcript 1 (Ecat1), embryonic stem cell-specific gene 1 (Esg1), sex determining region Y-box 2 (Sox2), paired box protein 6 (Pax6), stem cell antigen 1 (SCA-1), cluster of differentiation protein 29 (CD29), cluster of differentiation protein 34 (CD34), cluster of differentiation protein 90 (CD90), B1 integrin, tyrosine-protein kinase (cKit), surfactant protein C (SP-C), Clara cell 10 protein (CC10), splicing factor 1 (SF1), dosage-sensitive sex reversal gene 1 (DAX1), and superior cervical ganglion-10 protein (SCG10), in a carrier, wherein the cells are obtained by a process comprising isolating a viable population of spore-like cells from mammalian tissue or cell containing fluid following oxygen deprivation for at least four hours and culturing the cell in basic media for a time effective for expression of the one or more markers.

2. The composition of claim 1, wherein the carrier comprises a physiological buffer.

3. The composition of claim 1, wherein the carrier comprises a hydrogel.

4. The composition of claim 1, further comprising a biocompatible support structure.

5. The composition of claim 4, wherein the support structure is selected from the group consisting of a sponge, foam, coral, and a mesh.

6. The composition of claim 1, wherein the cells further express a gene encoding a protein selected from the group consisting of factor 8, vascular endothelial growth factor and cystic fibrosis transmembrane conductance regulator.

7. A method of treatment, comprising administering the composition of claim 1 to a subject in need thereof.

8. The method of claim 7, comprising administering the cells within damaged tissue in the subject.

9. The method of claim 8, wherein the damaged tissue is selected from the group consisting of a burn, a bone fracture, a torn ligament, an atrophied muscle, an ischemic heart and a malfunctioning gland.

10. The method of claim 7, wherein the cells are administered using a syringe or catheter.

* * * * *